United States Patent [19]

Berggren et al.

[11] Patent Number: 5,783,205
[45] Date of Patent: *Jul. 21, 1998

[54] INJECTABLE DRUG DELIVERY SYSTEM AND METHOD

[75] Inventors: Randall G. Berggren, Livermore; David J. Enscore, Saratoga; Susan M. Marks, San Jose; James L. Osborne, Mountain View; Patrick S.-L. Wong, Palo Alto; Wouter E. Roorda, Newark, all of Calif.

[73] Assignee: ALZA Corporation, Palo Alto, Calif.

[*] Notice: The term of this patent shall not extend beyond the expiration date of Pat. No. 5,620,700.

[21] Appl. No.: 843,682

[22] Filed: Apr. 10, 1997

Related U.S. Application Data

[63] Continuation of Ser. No. 437,471, May 9, 1995, Pat. No. 5,620,700, which is a continuation of Ser. No. 923,275, Jul. 31, 1992, abandoned, which is a continuation-in-part of Ser. No. 605,863, Oct. 30, 1990, abandoned.

[51] Int. Cl.$^6$ .............................. A61F 2/02; A61K 6/00
[52] U.S. Cl. .............................. 424/426; 424/435; 523/105; 523/113
[58] Field of Search .............................. 424/426, 435; 523/105, 113

[56] References Cited

U.S. PATENT DOCUMENTS

| 4,764,377 | 8/1988 | Goodson et al. | 424/435 |
| 5,620,700 | 4/1997 | Berggren et al. | 424/435 |

Primary Examiner—Carlos Azpuru
Attorney, Agent, or Firm—Steven F. Stone; Mary Ann Dillahunty

[57] ABSTRACT

The present invention is directed to a material which can be used to deliver a drug, such as an antibiotic, into a diseased tissue pocket, such as a periodontal pocket. The material is preferably a bioerodible oligomer or polymer. The oligomer or polymer containing the drug is heated and is then delivered, preferably by injection, into the tissue pocket at a physiologically compatible elevated temperature. Once the bioerodible material is injected into the pocket, the material cools to the body temperature of the pocket. As it cools, the material hardens and remains in place in the tissue pocket. The hardened material bioerodes in the pocket and releases the drug over a period of several days.

10 Claims, 3 Drawing Sheets

INJECTABLE DRUG DELIVERY SYSTEM AND METHOD

RELATED APPLICATIONS

This application is a continuation of U.S. Ser. No. 08/437,471 filed May 9, 1995, now U.S. Pat. No. 5,620,700, which is a continuation of U.S. Ser. No. 07/923,275 filed Jul. 31, 1992, now abandoned, which is a continuation-in-part of U.S. Ser. No. 07/605,863, filed Oct. 30, 1990, now abandoned.

TECHNICAL FIELD

This invention relates to a device and method for delivering a drug to a localized body site. More particularly, this invention relates to a device and method for delivering a drug, such as an antibiotic, to a diseased tissue site, such as a periodontal pocket, for the treatment of periodontal disease.

BACKGROUND ART

Periodontal disease is a common and widespread disease which has been shown to be a result of pathogenic bacterial infection established within the gingival sulcus. This condition, if not arrested, will cause formation of a periodontal pocket. The bacteria found in the periodontal pocket are more anaerobic and contain more gram-negative organisms than bacteria found supragingivally.

Conventional therapy and treatment of periodontal disease in humans involves the mechanical removal of bacterial plaque and other accumulated debris from the periodontal pocket, often called root planing and scaling. More severe cases may require periodontal surgery to remove damaged tissue. These procedures are expensive, painful, cause extensive bleeding and, accordingly, are not well accepted by patients. These procedures are also temporary at best, and frequent recall visits to the dental surgeon are often necessary.

Several factors reduce the effectiveness of supragingival application of drugs or other medicaments in treating periodontal disease. For example, the close proximity of the gum tissue to a tooth impairs diffusion of a medicament into a periodontal pocket. Also, a crevicular fluid is continually produced in the pocket and flows outwardly. The crevicular fluid flows out of the pocket at a rate of about 1 to 5 microliters per hour in healthy periodontal tissue and at a rate of about 10 to 100 microliters per hour in diseased periodontal tissue.

As a result, the penetration of topically or supragingivally applied medicaments has been largely ineffective in the treatment of periodontal disease. With topical application, the medicaments penetrate no more than about 2 mm into a periodontal pocket and are quickly washed out by the crevicular fluid outflow. Since periodontal pockets can be about 5 mm or greater in depth, topical application does not provide an effective means for treating diseased periodontal pockets.

Many techniques have been proposed for treatment of periodontal disease, e.g. drug-containing lozenges which slowly dissolve in the mouth, drug-containing chewing gums, topical buccal bandages and dressings, topically applied compositions (e.g., waxes, pastes, creams and ointments) and drug-impregnated dental floss. These techniques, however, are not effective in delivering a drug into a diseased periodontal pocket for the reasons outlined above.

Systemic application of drugs such as tetracycline for the treatment of periodontal disease is also known. Unfortunately, the systemic application of an antibiotic results in very low concentrations of antibiotic delivered to the diseased site (e.g., the periodontal pocket). There is also a greater opportunity for an adverse systemic reaction to a drug administered systemically compared to localized administration.

In order to overcome the disadvantages of topical treatments and systemic administration of antibiotics in order to treat periodontal disease, drug delivery devices suitable for placement directly in the periodontal pocket have been developed. For example, U.S. Pat. No. 4,568,535 discloses a delivery device comprising an ethylcellulose film containing metronidazole which is placed in a periodontal pocket for a period of days during which the metronidazole is slowly released. After the metronidazole is released, the film must then be surgically removed from the pocket. Antibiotic (e.g., tetracycline) containing fibers have also been inserted into the periodontal pocket to treat periodontal disease. See, for example, U.S. Pat. No. 4,175,326. After the antibiotic has been completely delivered, the fibers must be removed, requiring a follow-up visit to the dentist. In addition, the placement of fibers in the periodontal pocket has been found by certain individual practitioners to be somewhat time-consuming, thereby raising the cost of the treatment.

In response to these problems, bioerodible drug delivery devices have been proposed for treating periodontal disease. The delivery device typically includes an antibiotic dispersed in a bioerodible and biocompatible material. The device has a size and shape suitable for insertion into the periodontal pocket (e.g., in the shape of a fiber; see U.S. Pat. No. 4,764,377). The bioerodible material may be polymeric and it may be natural (e.g., collagen) or synthetic (e.g., a polylactide). After insertion into the periodontal pocket, the antibiotic is released slowly over a period of days. Following delivery of the drug, the material erodes and the erosion products are washed out of the pocket by the normal outflow of gingival fluid. Typically, the erosion products are swallowed and eventually excreted by the body. Since the material erodes in-situ within the periodontal pocket, there is no need for a follow-up visit to the dental surgeon in order to remove the drug delivery device.

While the use of bioerodible delivery devices represents a major step forward in the treatment of periodontal disease, there remains a need in the art for a device which can be more quickly and easily placed in a tissue pocket, such as a periodontal pocket, and will conform more exactly to the size and shape of each individual pocket for the release of a beneficial agent in order to treat a disease condition.

Baker in U.S. Pat. No. 4,780,320 describes a system for delivering drug to a periodontal pocket which comprises drug-containing biodegradable microparticles or microcapsules in a fluid carrier medium which are injected into the pocket with a syringe. These small particles, however, have several disadvantages when used in a tissue pocket. When they are inserted into body cavities such as a periodontal pocket, the eye or the vagina where there is considerable fluid flow, these small particles are poorly retained because of their small size and discontinuous nature, particularly when present in a fluid medium, and can easily be squeezed or flow out of the tissue pocket opening. A further limitation to the use of microparticles is their lack of reversibility without extensive intervention. That is, if there are complications after they have been injected, it is considerably more difficult to remove them from the body than with more solid implants.

Bucalo in U.S. Pat. Nos. 3,982,537, 4,030,499 and 4,054,138 describes a material formed of hydrogenated vegetable oil or animal fat for implanting into internal tissue. The hydrogenated oil/fat melts upon heating to a temperature of about 130° F. (55° C.). The material is mixed with the drug or antibiotic and injected into the internal tissue in a molten state. Once the material is injected, it cools to body temperature and hardens to a soft pliable solid material. The material eventually dissolves over time and is absorbed into the surrounding tissues. Unfortunately, this material has several disadvantages. The hydrogenated vegetable oil or animal fat is not well suited for retention in a periodontal pocket, which is not an internal tissue but has a large opening that communicates with the exterior environment. There is a natural tendency for gum tissues surrounding the roots of teeth to exert pressure thereon. As a result, soft pliable fats and oils can be quickly squeezed out through the opening of the periodontal pocket. This condition is exacerbated by normal patient activity such as chewing and swallowing, resulting in the material being squeezed out of the pocket before the drug delivery regimen can be completed. Additionally, the materials of Bucalo must be absorbed into the surrounding body tissue, which greatly limits the choice of materials that can be used.

Wahlig et al. in U.S. Pat. No. 4,853,225 describe polysaccharide implants which can be liquids at temperatures above body temperature and gels at body temperature. However, polysaccharides are a natural food source for bacteria, thus providing a substrate for bacterial growth. As a result, compositions comprising polysaccharides are not good choices for use in a body tissue pocket open to the environment, particularly to pockets in the mouth where large numbers of bacteria are continuously being introduced. Additionally, the viscosities of gellated polysaccharides are relatively low, and polysaccharide implants would tend to flow or be squeezed out through the opening of a body tissue pocket.

Dunn et al. in U.S. Pat. No. 4,938,763 describes biodegradable polymeric implants that are formed in-situ in the body. The polymer is placed into the animal in liquid form and cures to form the implant in-situ. This is done either by 1) a thermoplastic system formed by dissolving a non-reactive polymer in biocompatible solvent to form a liquid, placing the liquid within the animal, and allowing the solvent to dissipate to produce the implant; or by 2) a thermosetting system formed by mixing together a liquid acrylic ester-terminated, biodegradable prepolymer and a curing agent, placing the liquid mixture within an animal, and allowing the prepolymer to cure to form the implant. However, these systems are inconvenient to use in that they must be mixed at the time of implantation, resulting in additional steps and extra time for the doctor or technician, and then must be placed immediately into the pocket before the polymer cures and solidifies.

Thus, there has been a need in the art for a drug delivery platform which can be quickly and easily placed in a tissue pocket, such as a periodontal pocket; which is not easily expelled from the pocket by physiological conditions such as fluid flow or normal patient activities, such as chewing and swallowing; and which erodes in-situ within the pocket.

SUMMARY OF THE INVENTION

Accordingly, it is an object of the present invention to provide a drug delivery device which is effective to deliver a drug, such as an antibiotic, into a diseased tissue pocket, such as a periodontal pocket.

It is a further object of the present invention to provide a delivery device which can be easily and quickly inserted into a diseased tissue pocket by a medical technician and which preferably requires no follow-up visit to remove the device.

It is yet another object of the present invention to provide a delivery device which will remain in a diseased tissue pocket, such as a periodontal pocket, for an extended period of time without being expelled.

These and other important objects are met by the present drug delivery device and method. The drug delivery device comprises a drug-containing matrix material which when placed in a diseased tissue pocket releases the drug at a therapeutically effective rate over a predetermined drug delivery period. The matrix material is heated to soften the material to a point where it becomes flowable and can be delivered at a physiologically compatible elevated temperature into a biological pocket. Once the drug-containing matrix material is introduced into the pocket, the material cools into a less- or non-flowable drug-containing matrix that is retained within the pocket. Because of the flowability imparted by heating, it is often not necessary to incorporate a plasticizer into the matrix to make it flowable.

Once delivered, preferably by injection, into the biological pocket, the matrix cools to the body temperature of the host animal. At this temperature, the viscosity of the matrix is sufficiently high that the matrix is not displaced by the crevicular outflow or by normal patient activity such as chewing and swallowing.

Where the matrix material is bioerodible, the matrix material will bioerode, that is, it will break down or dissolve over a period of time from a unit structure into smaller entities that can be expelled from the biological pocket. This will usually occur at a point at or after completion of the treatment period. Where the matrix material is non-bioerodible, the matrix will be removed from the tissue pocket after the specified treatment period is completed.

The method of the present invention is particularly useful to heat high-viscosity oligomer or polymer formulations so that the viscosity drops in response to heating and softens to produce a flowable, injectable formulation which returns to its higher viscosity upon cooling to the temperature of the biological pocket. The formulation cools to a more viscous consistency with sufficient cohesiveness to be retainable in the biological pocket (possibly with the addition of a biocompatible adhesive), unlike gels or solutions or other fluids.

According to a preferred embodiment of the present invention, the diseased biological pocket comprises a periodontal pocket and the drug comprises an antibiotic. The matrix material is preferably a bioerodible polymer selected from polylactic acid, polyglycolic acid, copolymers of lactic acid and glycolic acid, polylactide-co-glycerate, polyglycolide-co-glycerate and poly(orthoesters), or a bioerodible oligomer selected from oligomers of hydroxycarbonic acids and oligomers of glycolic acid and/or lactic acid and their derivatives with alcohols and/or carbonic acids.

The term "physiologically compatible elevated temperature" as used herein means a temperature that is above the natural body temperature of the animal receiving the device and that will not normally cause damage to the tissues at the site of implantation. For example, in humans, a physiologically compatible temperature in tissues such as the periodontal pocket is generally between about 38° and about 75° C., preferably between about 38° and 55° C. and most preferably within several degrees of body temperature (e.g., about 38°–45° C.).

The terms "tissue pocket" and "biological pocket" refer to a naturally occurring pocket in the body of an animal having an opening to the external environment.

DETAILED DESCRIPTION OF THE INVENTION

Figure 1:
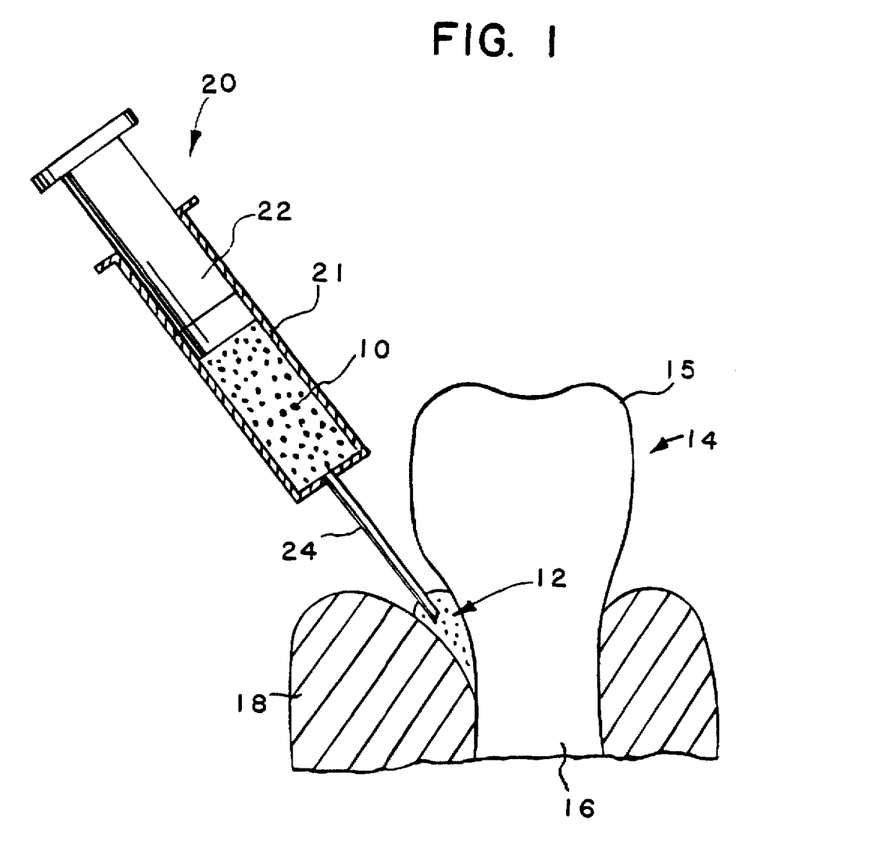
FIG. 1 is a side view, shown partly in section, of a diseased periodontal pocket and illustrates a preferred method of placing the drug delivery device of the present invention into a periodontal pocket.

A preferred method of placing the drug delivery device of the present invention into a periodontal pocket is shown in FIG. 1. The periodontal pocket is designated by the numeral 12 and comprises a cavity formed between a tooth 14 and the adjacent gum 18. As the diseased condition progresses, the pocket 12 progressively deepens along the root 16 of tooth 14. Without treatment, the gum 18 will progressively detach from the root 16 and allow bacteria to reach the root 16 until the tooth is loosened and eventually lost.

In order to treat the diseased periodontal pocket 12, an antibiotic-containing matrix material 10, which material has been heated to a physiologically compatible elevated temperature so that it is initially in the form of a viscous fluid, is injected into the pocket 12 using a syringe 20. The syringe 20 comprises a cartridge 21, a sliding plunger 22 and a hollow needle 24 having a length suitable for reaching the periodontal pocket 12. Typically, needle 24 will have an inner diameter in the range of from about 0.2 to about 1.5 mm.

In order for the material 10 to be injected through the hollow needle 24, it should have a dynamic viscosity of less than $1 \times 10^6$ poise (at 0.1 radian/sec), and preferably less than about $5 \times 10^5$ poise (at 0.1 radian/sec), when measured at a physiologically compatible elevated temperature. However, once the material 10 is introduced into the periodontal pocket 12, it is desirable for the material 10 to set up or solidify in order to insure that it is not washed out by the crevicular fluid flowing out of pocket 12. That is, it should have a dynamic viscosity, at the body temperature of the periodontal pocket, of greater than about $1 \times 10^6$ poise (at 0.1 radian/sec) and preferably greater than about $5 \times 10^6$ poise (at 0.1 radian/sec).

The drug-containing matrix materials of the present invention are flowable (that is, the material can be poured into a container and will conform to the shape of the container) when the material is heated to a physiologically compatible elevated temperature and less- to non-flowable (that is, the material sets up and will not easily flow out of the container) when the material is at the body temperature of the host animal. The drug-containing materials used in the present invention should preferably have a viscosity which is sufficiently low when heated at a physiologically compatible elevated temperature to allow the material to be injected using a syringe when the material is at such elevated temperature but which is sufficiently high at body temperature to remain in the biological pocket. Additionally, the viscosity at body temperature should not be so high that the material is very hard and brittle, causing discomfort to the host and possible damage to the surrounding tissues. It has been found that those materials having a dynamic viscosity of less than about $1 \times 10^6$ poise at 0.1 radian/second are sufficiently low in viscosity to be injected with a syringe. Thus, the materials chosen as the matrix in the present invention must have a viscosity less than about $1 \times 10^6$ poise at 0.1 rad/sec when heated to a physiologically compatible elevated temperature and greater than about $1 \times 10^6$ poise when at body temperature.

The matrix material 10 is biocompatible (e.g., it should not be toxic or otherwise cause adverse tissue reactions) and can be either bioerodible or non-bioerodible. The term "bioerodible" is used herein to mean materials which are broken down into innocuous low molecular weight species by substances found in the body, such as water, enzymes or bacteria, and then excreted by the body. The matrix material is also non-toxic, non-carcinogenic, and causes no adverse immunologic response.

The bioerodible matrix material is typically a natural or synthetic oligomer or hydrophobic polymer, although cross-linked hydrophilic polymers are generally suitable for the purposes of the present invention. The matrix material should be able to maintain its structural integrity for at least about 1 day after placement in a tissue pocket, preferably for at least about 7 days and more preferably for at least about 10 days after placement in a pocket.

Representative natural bioerodible materials include naturally occurring polymers such as cross-linked collagen, agar—agar, cross-linked gelatin, glycerin, polysaccharides and sugar phosphates.

Examples of bioerodible synthetic polymers include poly (lactic acid) and polyglycolic acid, or their derivatives; polylactides; polyglycolides; copolymers of lactides and glycolides; oligomers of glycolic acid and/or lactic acid and their derivatives with alcohols and/or carbonic acids; polylactide-glycerate; polyglycolide-co-glycerate; polyamides; polyesters; oligomers of hydroxycarbonic acids; poly (ortho)esters; polycaprolactones; polyanhydrides; pyrrolidones (e.g., methylpyrrolidone); and cross-linked cellulosic polymers (e.g., carboxymethyl cellulose). Mixtures and combinations of these may also be used.

One presently preferred type of bioerodible synthetic polymer for use in this invention comprises poly(lactic acid), poly(glycolic acid) and copolymers of lactic and glycolic acid.

Useful poly(lactic acids) include both homopolymers of lactic acid and/or lactides and copolymers of lactic acid (and/or lactides) and glycolic acid (and/or glycolides). Particularly preferred copolymers contain from about 25 to 75 mol % lactic acid units and about 25 to 75 mol % glycolic acid units. Usually, poly(lactic acids) are prepared from the cyclic esters of lactic acids. Both L(+) and D(−) forms of lactic acid may be used to prepare the poly(lactic acid) as well as the optically inactive DL-lactic acid mixture or any desired mixtures of D(−) and L(+) lactic acids.

Lactic acid copolymers provide flexibility in choosing the life of a polymer matrix since this can be controlled through the amount and type of comonomer used. Some illustrative examples of suitable comonomers include glycolide, glycerate, β-propiolactone, tetramethylglycolide, β-butyrolactone, tetramethylglycolide, β-butyrolactone, γ-butyrolactone, piyalolactone, and intermolecular cyclic esters of α-hydroxybutyric acid, α-hydroxyisobutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-β-methylvaleric acid, α-hydroxyheptanoic acid, α-hydroxyoctanoic acid, α-hydroxydecanoic acid, α-hydroxymyristic acid, α-hydroxystearic acid, α-hydroxylignocenic acid, and α-phenyllactic acid. A presently preferred copolymers is polylactide-co-glycolide.

Poly(lactic acids) are well known in the art and methods of preparing poly(lactic acids) are well documented in the literature.

Poly(glycolic acids) have also been found to possess excellent biodegradable properties. Poly(glycolic acid) is the homopolymer of glycolic acid (hydroxyacetic acid). In the conversion of glycolic acid to poly(glycolic acid), glycolic acid is initially reacted with itself to form the cyclic ester glycolide which, in the presence of heat and a catalyst, is converted to a high molecular weight linear-chain polymer. Poly(glycolic acids) and their properties are well known in the art. Glycolic acid copolymers may be prepared utilizing suitable comonomers such as lactide and those listed above with reference to lactic acid copolymers.

A further preferred group useful as matrix materials are oligomers of glycolic acid and/or lactic acid and-their derivatives with mono- and/or polyfunctional alcohols, glycerol being one example, and/or carbonic acids, as described in European patent publications EP 290,983 and EP 352,588.

Another preferred type of matrix materials are the polyester oligomers of hydroxycarbonic acids, as described in European patent No. EP 100,981.

Poly(orthoesters) may also be used as the matrix material. Suitable poly(orthoester) polymer matrices for delivering a drug to a diseased tissue pocket, and methods for making such matrices, are disclosed in U.S. Pat. Nos. 4,066,747; 4,070,347; 4,093,709; 4,119,579; 4,131,648; 4,136,252; 4,138,344; 4,155,740; 4,155,992; 4,180,646; 4,186,185; 4,322,323; and 4,346,709; the disclosures of which are incorporated herein by reference. The poly(orthoester) polymers may be selected from those available from ALZA Corporation (Palo Alto, Calif.) under the trademark Alzamer® and can include homopolymers, as well as copolymers and mixtures or blends of two or more poly (orthoesters). Presently preferred poly(orthoester) polymers are poly(2,2-dioxocyclohexanedimethylene tetrahydrofuran) ("POE-1") and polymeric mixtures or blends of poly(2,2-dioxocyclohexanedimethylene tetrahydrofuran) ("POE-1") and poly(2,2-dioxohexamethylene tetrahydrofuran) ("POE-2").

A homopolymer of POE-1 of high molecular weight possesses a high viscosity, whereas POE-1 of lower molecular weight will be of a lower viscosity. POE-1 homopolymers for use in the present invention are, therefore, chosen from those with molecular weights falling within the range that will give the desired viscosity for the practice of the invention. Alternately, high and low molecular weight POE-1 polymers may be combined to provide mixtures having the desired viscosity. By high molecular weight is meant POE-1 of about 30,000 to greater than 60,000 Mw, and by low molecular weight is meant POE-1 of about 2,000 to about 10,000 Mw.

The matrix material of the present invention additionally can be selected from physical mixtures of POE-1 and POE-2, block copolymers of POE-1 and POE-2, and random compolymers of POE-1 and POE-2. There are several methods of preparing such matrix materials. The two different polymers can be physically mixed together after polymerization (physical mixture); they can be physically mixed together as low molecular weight block polymers and then polymerized further (block copolymers); or segments of the two polymers, i.e. the diol fractions, can be-mixed in the desired ratio and be reacted together with diethoxytetrahydrofuran and polymerized (random copolymers). These methods are explained in detail in the above referenced patents. By varying the ratio of POE-1 to POE-2 in a polymer mixture, the viscosity of a formulation can be controlled. The POE-1/POE-2 polymeric mixtures can contain from about 10 to 90 wt % POE-1 units and from about 90 to 10 wt % POE-2 units. For example, a blend of the two polymers in a 90:10 POE-1:POE-2 ratio will be highly viscous and is formed into the desired shape by extrusion or melt pressing, whereas a blend of 10:90 POE-1 to POE-2 will be of low viscosity and can be injected at room temperature. Preferably, in the practice of the present invention, the ratio is of from about 25:75 to about 75:25 of POE-1 to POE-2, and more preferably it is from about 40:60 to about 60:40. In the same manner, blends of high molecular weight (Mw) POE-1 and low molecular weight (Mw) POE-1 in varying ratios may be formed to provide the desired viscosities. The range of high Mw to low Mw POE-1 is from about 90:10 to 10:90, preferably from about 25:75 to about 75:25, and more preferably from about 30:70 to about 50:50. Thus, it is possible to provide a range of disease therapy platforms by a careful choice of the appropriate weight ratio of poly(ortho)ester polymers. However, at the same time, the polymer matrix must not only be of a flowability that is suitable for injection into a periodontal or other biological pocket at injection temperature but also of a viscosity that allows the matrix to remain within the pocket at pocket temperature for an extended period of time without being expelled. These two contradictory physical requirements necessitate a very careful choice of the particular ratio of POE-1 to POE-2, or of high Mw POE-1 to low Mw POE-1, in the polymer matrix blend.

Various non-bioerodible polymers may be utilized as the matrix material in the present invention. The basic requirements are that the viscosity of the polymer fall within the appropriate range at body temperature and at a physiologically compatible temperature and that the material be biocompatible in the environment of use. When a nonerodible material is used as the matrix, it is necessary for the implant to be removed from the tissue pocket after the drug has been dispersed from the matrix.

The drug incorporated into the matrix material of the present invention may be of various types such as antibiotics, anti-inflammatory drugs, growth factors, local anesthetics and anti-caries agents, for example. When the material is injected into a diseased periodontal pocket, the drug typically comprises an antibiotic. The antibiotic may be of various types. For example, useful antibiotics include, but are not limited to, tetracyclines, penicillins, cephalosporins, oxytetracyclines, chlorotetracycline, minocycline, metronidazole, chloramphenicol, chlorhexidine, streptomycin, neomycin, doxycycline, quinolines (e.g., quinoline salicylate, quinoline tartrate), macrolides (e.g., erythromycin, streptomycin), ciprofloxacin, sulfonamides, phenolics, mercurials, quaternary ammonium compounds, chlorhexidine, sanguinarine, and mixtures thereof. In addition to mixtures of two or more antibiotics, mixtures of an antibiotic with another drug may also be used, such as, for example, an anti-inflammatory drug such as aspirin, salicylamide, naproxen, indomethacin, fenoprofen, indoprofen, ibuprofen, carprofen, and diclofenac; local anesthetics such as lidocaine, novocaine, bupivacaine, and procaine amide; or anti-caries agents such as sodium fluoride.

The amount of drug that is present in the delivery device, and that is required to achieve a therapeutic effect, depends on many factors, such as the particular drug selected, the minimum necessary dosage of the drug, the permeability of the matrix material to the drug, the rate of erosion of the matrix, and the period of time for which the drug is to be delivered in the pocket. Generally, the amount will vary, for example, from about 1 to about 60% by weight, preferably from about 10 to about 40 wt %, and more preferably from about 15 to about 30 wt %. The minimum amount of each drug is determined by the requirement that sufficient quantities of drug must be present in the device to maintain the desired rate of release over the given period of application. The drug may be soluble or miscible in the matrix material, although this is not absolutely required so long as the drug is slowly released from the material over the desired period of time. When treating periodontal pockets having a pocket size of about 50 microliters, for example, it is preferable to place a delivery device therein which contains from about 2 to about 100 mg of a drug such as an antibiotic. Preferably, the drug is uniformly distributed in the matrix material.

After placement in the biological pocket, the drug is slowly released from the matrix material into the pocket so as to maintain an effective concentration of the drug in the pocket for the desired period of time. The drug is releasably contained in the matrix material in a manner such that the drug is slowly released from the material into the biological pocket. The drug slowly releases from the matrix material in a manner such that an effective concentration of the drug in the pocket is maintained for a predetermined period of time, such as, in the case where the drug is an antibiotic and the pocket is a periodontal pocket, for a period of about 1 to about 30 days, preferably about 7 to 21 days. In this manner, the antibiotic reduces periodontal pathogenic bacteria (such as *Bacteroides gingivalis* and many other types of bacteria) and also reduces inflammation. This is much more effective than a simple application of antibiotic alone to the pocket. The amount of antibiotic placed in a pocket can be determined so that the desired amount is released over the desired time period.

The delivery device of the invention may also optionally include an amount of a plasticizer to alter the viscosity of the matrix material so that it falls within the range required by the present invention. Whether a plasticizer is included will depend on the matrix material that is used. For example, when certain copolymers of lactic acid and glycolic acid are used, it is desirable to include a plasticizer to keep the material from becoming too hard and brittle after it has cooled to body temperature. On the other hand, a plasticizer is often not required when mixtures of poly(orthoesters) are utilized as the matrix material. Suitable biocompatible plasticizers include, but are not limited to, triethyl citrate, acetyl triethyl citrate, tributyl citrate, acetyl tributyl citrate, triethyl glycerides, triethyl phosphate, diethyl phthalate, diethyl tartrate, mineral oil, polybutene, silicone fluid, glycerin, ethylene glycol, polyethylene glycol, ethyl lactate, propylene glycol, propylene carbonate, ethylene carbonate, butyrolactone, triacetin, diacetin, ethylene oxide and propylene oxide. In presently preferred embodiments, the plasticizer is chosen from triethyl citrate and propylene carbonate. When a plasticizer is included in the matrix material, it is generally present in an amount of from about 5 to about 30 wt %, preferably from about 7 to about 20 wt %.

In addition to the drug and, optionally, a plasticizer, the matrix may also contain drug release-rate regulating agents, dyes, pigments, inert fillers, stabilizers, excipients and other conventional components of pharmaceutical products or oligomeric or polymeric systems known to the art.

The devices and methods of the present invention are useful generally for the treatment of periodontal infections such as periodontitis and irritated gums such as gingivitis. These diseases occur below the gingival margin in the periodontal pocket or along the gum line.

The drug delivery devices described herein are in the form of a gel or viscous fluid when at a physiologically compatible elevated temperature which allows insertion or injection into the periodontal pocket by means of a syringe, and are in the form of a more viscous, less- to non-flowable mass which will remain in the periodontal pocket when at the body temperature of the host animal. Heating to the desired elevated temperature may be effected by a number of methods and sources of heat, such as a hotwater bath, a hot plate, an oven or a microwave oven. The matrix material may be heated prior to placing it in an injection device or after such placement. In one preferred method of the invention, the matrix material is heated with the use of an injection device such as a syringe or a trocar which has a heated compartment adapted to contain the matrix material and a means of applying controlled pressure to the material in the compartment, such as a piston or plunger, to eject the material through a needle into the site of treatment. Examples of heated syringes are included in U.S. Pat. No. 4,030,499. In use, the matrix material is placed into the compartment, which compartment is then heated by electrical or other means for a period of time until the material has reached the desired temperature and viscosity. Pressure is then applied by hand or through mechanical means to eject the heated material into the treatment site, such as a periodontal pocket. The needle itself may or may not be heated as well. When the needle is not heated, the temperature to which the material is heated in the compartment may be greater than the-desired application temperature to compensate for any cooling that takes place as the material is transported through the unheated needle to the treatment site.

In another presently preferred embodiment of the invention, the matrix material is placed in a pre-measured amount into a cannula, at a point in time prior to application into the tissue pocket. This provides a convenient means for having the material in a ready-to-use form at the time of application. At the time of application, the filled cannula is heated to the desired physiologically compatible elevated temperature, and is then placed onto the end of an applicator, which then delivers the heated matrix material from the cannula into the tissue pocket. One such device which may be used is the Ultrafil® applicator and its cannulas (The Hygenic Corporation, Akron, Ohio).

The injection procedure can be performed rapidly and efficiently. The material penetrates to the bottom of the periodontal pocket so that the anaerobes in the pocket are exposed to the antibiotic as it is released from the matrix. No strings, fibers or films are used which must be stuffed into a pocket. When the material is bioerodible, the dentist does not have to remove the material after the antibiotic has been released in the periodontal pocket.

Another advantage of the delivery device of this invention is that it is injected into the diseased pocket in softened, flowable form, so that it completely fills, and therefore conforms exactly to the shape of, the pocket. An adhesive material may be added, if desired, to assist in holding the device in place within the pocket. After cooling to body temperature, the matrix material sets up and remains in the periodontal pocket and is not-dislodged by crevicular fluid flow or by normal patient activities such as chewing and swallowing.

The injectable matrices of the present invention may be used to treat biological pocket sites in the human body other than a periodontal pocket. For instance, the matrices of the present invention may be inserted within the sacs defined by the surface of the sclera of the eyeball and the conjunctiva of the eyelid. The matrices of the present invention may be introduced into the eye sacs from a conventional eye drop bottle, for example. Any of the drugs used to treat the eye and surrounding tissues can be incorporated into the matrix materials adapted for insertion into the ocular sacs. Also, it is practical to use the eye and surrounding tissues as a point of entry for systemic drugs or antigens that ultimately enter circulation in the blood stream, or enter the nasopharyngeal area by normal routes, and produce a pharmacologic response at a site remote from the eye. Thus, drugs or antigens which will pass through the eye or the tissue surrounding the eye to the blood stream or to the nasopharyngeal or the esophageal areas, but which are not used in therapy of the eye itself, can be incorporated in the matrix adapted for insertion in the eye sacs.

Suitable drugs for use in therapy of the eye with the ocular insert of this invention consistent with their known dosages and uses are, without limitation, antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antivirals, including idoxuridine; and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, fluocinolone, medrysone, prednisolone, methylpredenisolone, predisolone 21-phosphate, prednisolone acetate, fluoromethalone, betamethasone and triamcinolone; decongestants such as phenylephrine, naphazoline, and tetrahydrazoline; miotics and anticholinesterases such as pilocarpine, eserine salicylate, carbachol, diisopropyl fluorophosphate, phospholine iodide, and demecarium bromide; mydriatics such as atropine sulfate, cyclopentolate, homatropine, scopolamine, tropicamide, eucatropine, and hydroxyamphetamine; and sympathomimetics such as epinephrine.

The matrix materials of the present invention can also be used as an intravaginal drug delivery device. The heated matrix materials of the present invention can be introduced into the vagina using a syringe, a squeeze bottle or similar device. Once injected, the matrix material cools to body temperature and solidifies. Such a delivery platform is greatly preferred to the intravaginal creams and ointments known in the prior art which have a tendency to flow out of the vagina during use.

The matrices adapted for placement in the vagina may incorporate a number of drugs, including antibiotics and antifungal agents, for treating local and/or systemic conditions.

Oligomeric and polymeric matrices can be designed which have a wide variety of drug exudation rates and biodegradability: Bioerodible matrices can be synthesized to have lives shorter than, equal to or longer than the period of effective drug delivery. For shorter matrix lives, drug delivery will be accomplished by a combination of drug exuding from the matrix and matrix biodegradation; for longer matrix lives, the rate of drug delivery will be substantially dependent on only drug exudation from the matrix.

The molecular weight of poly(lactic acids) and polyglycolic acid are closely related to both the rate of exudation of drug from the matrix and the rate of biodegradation of the matrix. It has been found that high molecular weights, i.e. Mw=15,000 or higher, result in polymer matrices which retain their structural integrity for longer periods of time; while lower molecular weights, i.e. Mw=10,000 or below, result in a shorter matrix life.

Crystallinity also affects the exudation and biodegradability rates. Polymer matrices having higher degrees of crystallinity have slower exudation rates and slower biodegradability. It is known, of course, that crystallinity has a marked effect on physical properties. See, Flory, Principles of Polymer Chemistry, 5th printing, 1966, at pages 49 et seq. It has also been reported in the literature that gaseous diffusion through polymeric membranes is slower, in general, for those polymers having higher degrees of crystallinity than for those with lower degrees of crystallinity. See, Michaels and Bixler, "Flow of Gases through Polyethylene and Rubbery Polymers", J. Poly Sci., 50:413–439 (1961).

The rate at which drug is released from the bioerodible matrix material can be controlled by choosing appropriate molecular weights and degrees of crystallinity of the oligomer or polymer matrix. For example, if it is desirable to release drug into the pocket over a relatively long duration (e.g., 10 to 30 days), a high molecular weight polymer formed from a pure optical isomer of lactic acid can be used for the matrix. On the other hand, if a more rapid release rate over a shorter duration (e.g., 1 to 10 days) is desired, a low molecular weight lactic acid copolymer having a lower degree of crystallinity can be synthesized for use as the polymer matrix. It is also known that the rate at which drug is released from the matrix can be adjusted by varying the temperature or other conditions of matrix fabrication. Those skilled in the art will know or be able to determine by routine experimentation many suitable combinations of molecular weights, degrees of crystallinities, copolymers and mixtures of polymeric matrix materials, and matrix fabrication parameters such as the degree of plasticization to accomplish a desired release rate and duration.

The amount of drug released from the matrix material will depend to a great extent on the amount of drug-containing material which can be injected into the pocket. The amount of matrix material which can be injected into the pocket will in turn depend upon the size of the pocket. For example, assuming a periodontal pocket volume of 50 µL and further assuming that the pocket can be completely filled with an antibiotic-containing matrix material, the antibiotic is preferably released from the matrix material at a rate in the range of about 0.1 to about 2 mg per day. A rate of about 0.2 to about 1 mg per day is more preferred. If necessary, a drug release-regulating agent such as sodium chloride, maleic anhydride or xylitol can be added to assist in regulating the rate of release of the antibiotic. In the case of antibiotic delivery to a periodontal pocket, the antibiotic is preferably released from the matrix material over a period of from about 1 to 30 days, more preferably about 7 to 21 days, most preferably about 7 to 14 days. Since foreign objects placed in a periodontal pocket can actually induce periodontal disease, it is preferable in the practice of this invention to use a bioerodible material as the matrix material, and it is also preferred that the bioerodible matrix material should erode as soon as possible after the drug delivery regimen is completed. However, it is permissible for the bioerodible material to take a longer time period to be eroded.

The delivery device of the invention is useful in both animal and human subjects. Examples of animal subjects include dogs, cats and other animals (e.g., monkeys) which may be affected by eye and/or periodontal disease.

The drug delivery devices of the present invention are further illustrated by means of the following examples. These examples are merely illustrative of the present invention, and they should not be considered as limiting the scope of the invention in any way, as these examples and other equivalents thereof will become apparent to those versed in the art in light of the present disclosure, the drawings and the accompanying claims.

EXAMPLE 1

Into a 50 ml glass beaker was added 62 wt % of a copolymer of lactic acid and glycolic acid (PLGA), comprising 50 mol % lactic acid units and 50 mol % glycolic acid units and having an average molecular weight of 7,000. Also added to the beaker was 18 wt % of liquid triethyl citrate (Citroflex® 2) and 5 wt % of sodium chloride. The mixture was heated to a temperature of 50° C. and stirred for 5 minutes. Then, 15 wt % of tetracycline HCl was added to the mixture and stirred for an additional 5 minutes. The dynamic viscosity of the resulting formulation at various temperatures was measured (at 0.1 radian/sec) using a Rheometrics® model RMS-800 and are presented in Table A.

TABLE A

| | Dynamic Viscosity at 0.1 radian/sec. | | | |
|---|---|---|---|---|
| Example | 35° C. | 40° C. | 45° C. | 50° C. |
| 1 | $5 \times 10^4$ | $2.5 \times 10^4$ | $1 \times 10^4$ | $5 \times 10^3$ |
| 2 | $1.5 \times 10^5$ | $6 \times 10^4$ | $2.5 \times 10^4$ | $1.5 \times 10^4$ |
| 3 | $5 \times 10^5$ | $1 \times 10^5$ | $8 \times 10^4$ | $4 \times 10^4$ |
| 4 | $1.5 \times 10^6$ | $4 \times 10^5$ | $1.5 \times 10^5$ | $6 \times 10^4$ |
| 5 | $4 \times 10^6$ | $1 \times 10^6$ | $3 \times 10^5$ | $1.5 \times 10^5$ |
| 6 | $3 \times 10^5$ | $2 \times 10^5$ | $1.8 \times 10^5$ | $1.5 \times 10^5$ |
| 7 | $6 \times 10^5$ | $4.5 \times 10^5$ | $4 \times 10^5$ | $3.5 \times 10^5$ |
| 8 | $1.5 \times 10^6$ | $8 \times 10^5$ | $7 \times 10^5$ | $4.5 \times 10^5$ |
| 9 | $2 \times 10^6$ | $1.5 \times 10^6$ | $1 \times 10^6$ | $9 \times 10^5$ |
| 10 | $3 \times 10^6$ | $1.5 \times 10^6$ | $5.5 \times 10^5$ | $2.5 \times 10^5$ |
| 11 | $2 \times 10^6$ | $8 \times 10^5$ | $4 \times 10^5$ | $2.5 \times 10^5$ |

EXAMPLES 2–5

Following the procedure of Example 1, with the exception that the ratios of the PLGA to triethyl citrate are varied, the four formulations under Table B were prepared. The bioerodible material comprised the same copolymer used in Example 1. The dynamic viscosity of the formulations was measured (at 0.1 radian/sec) and is shown in Table A.

TABLE B

| Example | PLGA (wt %) | Triethyl citrate (wt %) | Tetracycline HCl (wt %) | NaCl |
|---|---|---|---|---|
| 2 | 65 | 15 | 15 | 5 |
| 3 | 68 | 12 | 15 | 5 |
| 4 | 70 | 10 | 15 | 5 |
| 5 | 72 | 8 | 15 | 5 |

EXAMPLE 6

To a beaker under an $N_2$ environment was added 4.5 g of high molecular weight POE-1 poly(orthoester) polymer (Mw=50,000) and 5.5 g of POE-2 poly(orthoester) polymer (Mw=35,500). The mixture was stirred at 110° C. for several minutes to give a 45/55 ratio mixture of POE-1/POE-2 polymer blend. The dynamic viscosity of the resulting formulation was measured as in Example 1, and the results are shown in Table A.

EXAMPLES 7–9

Following the procedure of Example 6, three polymeric formulations comprising different ratios of POE-1 to POE-2, as shown in Table C, were prepared. Their dynamic viscosities were measured, as in Example 1, and are presented in Table A.

TABLE C

| | Poly(orthoester) Ratio | |
|---|---|---|
| Example | POE-1 | POE-2 |
| 7 | 50 | 50 |
| 8 | 55 | 45 |
| 9 | 60 | 40 |

EXAMPLE 10

Following the procedure of Example 6, 5.0 g of high molecular weight POE-1 (Mw=55,000) and 5.0 g of low molecular weight POE-1 (Mw=3,200) were combined together to give a 50/50 polymeric mixture. The dynamic viscosity of the polymer was measured as in Example 1, and the results are presented in Table A.

EXAMPLE 11

Following the procedure of Example 6, 8.0 g of high molecular weight POE-1 (Mw=55,000) and 2.0 g of propylene carbonate were combined together to give a formulation with a ratio of 80/20 C101ct to propylene carbonate. The dynamic viscosity of the resulting polymer was measured and is presented in Table A.

EXAMPLE 12

The in vitro release of tetracycline HCl at 37° C. over time from the PLGA formulations of Examples 3, 4 and 5 was determined as follows.

Figure 2:
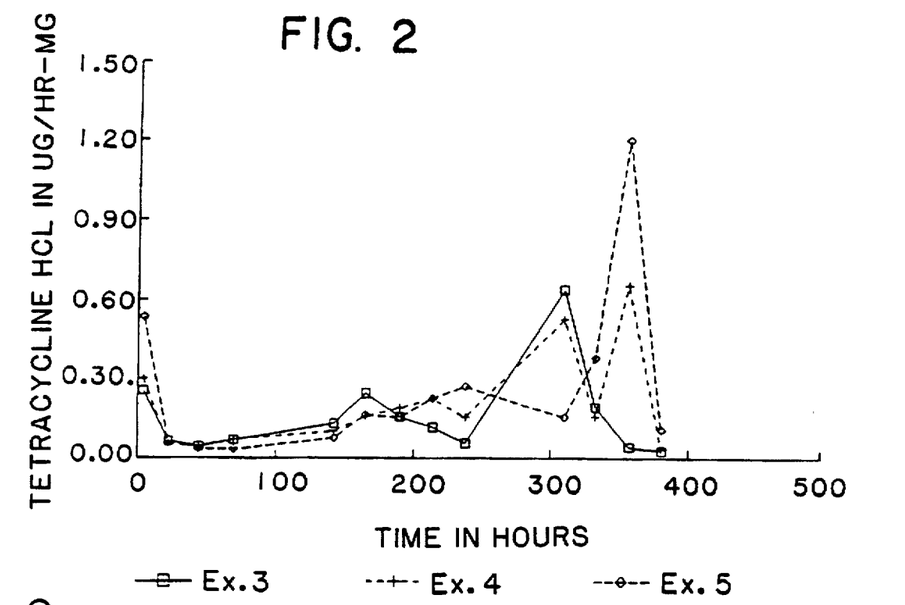
FIG. 2 graphically illustrates the in vitro release at 37° C. of tetracycline HCl over time from three polylactic/polyglycolic (PLGA) copolymer formulations of the invention.

0.5 Grams of the formulation to be tested was placed in a glass container, together with about 100 mL of distilled water. The jar was placed in a 37° C. water bath, after which samples of the distilled water were taken at regular intervals and replaced with new water. The drug content in each water sample was analyzed by UV spectrophotometry at 357 nm. The results are shown in FIG. 2.

EXAMPLE 13

Figure 3:
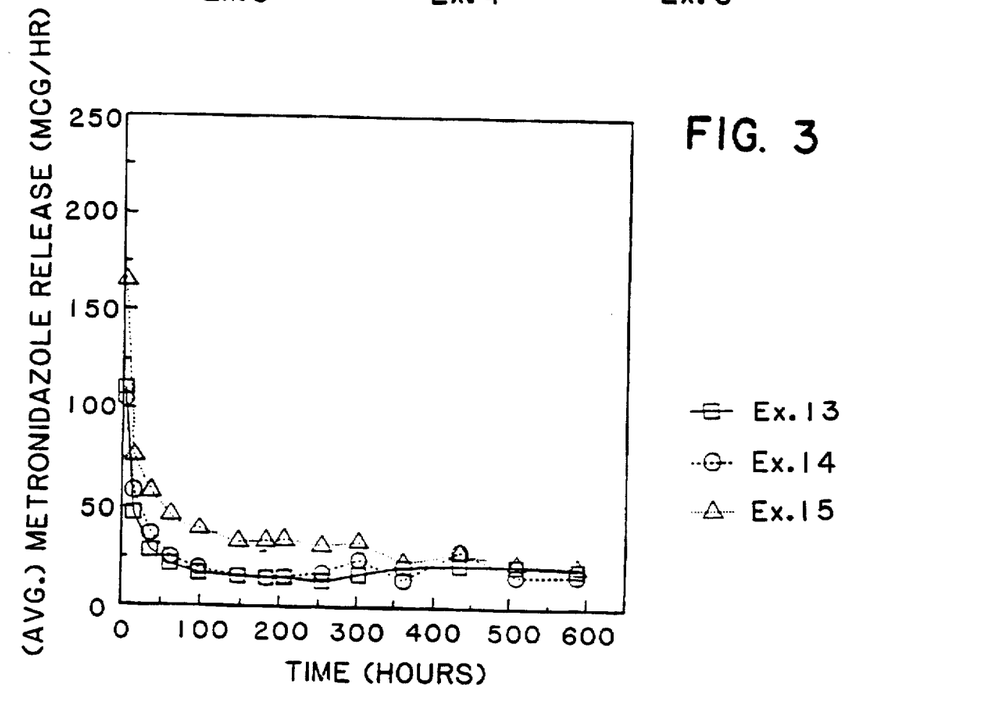
FIG. 3 graphically illstrates the in vitro release at 37° C. of metronidazole over time from three poly(ortho)ester formulations of the invention.

In a beaker, 48 wt % of high molecular weight POE-1, 32 wt % of POE-2, 20 wt % of metronidazole and 0.25 wt % of sodium carbonate (a stabilizer) were stirred together at 100° C. for 20 minutes. The in vitro release of metronidazole from the resulting 60/40 POE-1:POE-2 polymeric matrix at 37° C. was observed, following the procedure of Example 12, and the release rate profile is shown in FIG. 3.

EXAMPLES 14 and 15

Following the procedure of Example 13, the formulation of Example 13 was repeated, except that the ratio of POE-1 to POE-22 was changed to 55/45 (Ex. 14) or to 40/60 (Ex. 15). The in vitro release of the drug from these two formulations was measured and is presented in FIG. 3.

EXAMPLES 16 and 17

Figure 4:
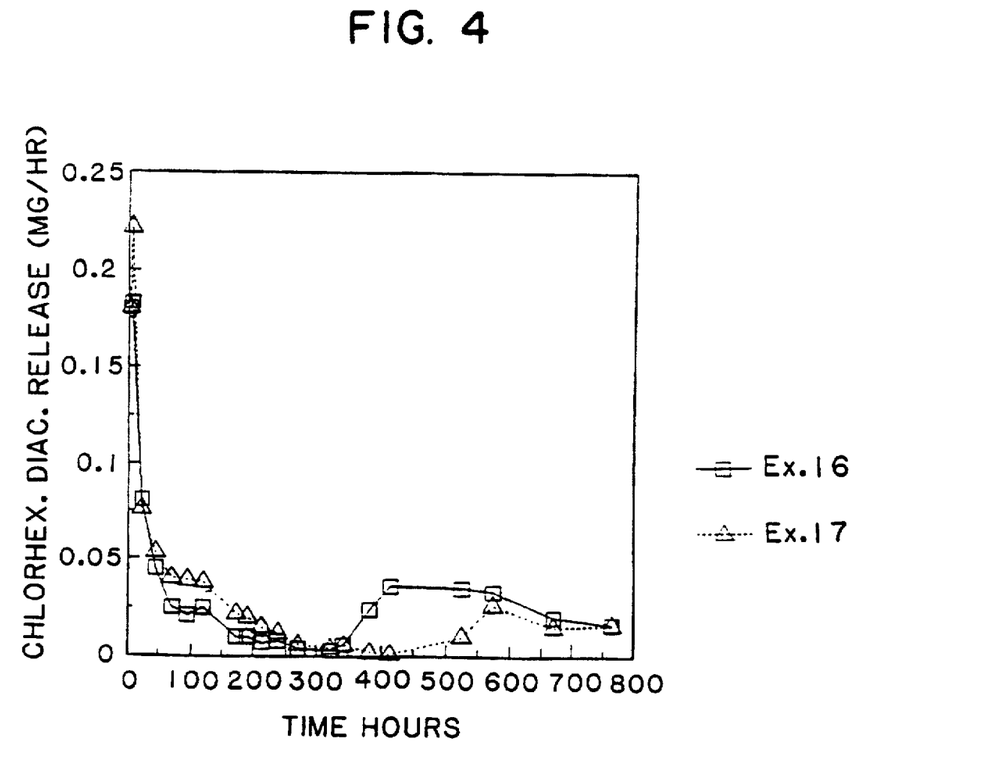
FIG. 4 graphically illustrates the in vitro release at 37° C. of chlorhexidine diacetate over time from two poly(ortho) ester formulations of the invention.

Following the procedure of Example 13, 42 wt % of high molecular weight POE-1, 28 wt % of POE-2, 20 wt % of chlorhexidine diacetate and 10 wt % of sodium chloride were mixed together to give a polymeric matrix having a 60/40 ratio of POE-1 to POE-2 (Ex. 16). In the same manner, 36 wt % of POE-1, 24 wt % of POE-2, 20 wt % of chlorhexidine diacetate and 20 wt % of sodium chloride were mixed together to give a matrix having a 60/40 ratio of POE-1 to POE-2 (Ex. 17). The in vitro release of the chlorhexidine diacetate from each of these formulations was measured and is presented in FIG. 4.

EXAMPLE 18

Following the procedure of Example 13, 32 wt % of high molecular weight POE-1 (Mw=55,000), 48 wt % of low molecular weight POE-1 (Mw=3,200), 20 wt % of metronidazole and 0.25 wt % of sodium carbonate were mixed together to give a metronidazole-containing polymeric matrix having a 40/60 ratio of high Mw POE-1 to low Mw POE-1.

EXAMPLE 19

Following the procedure of Example 13, 24 wt % of high Mw POE-1 (Mw=55,000), 36 wt % of low Mw POE-1 (Mw=3,200), 20 wt % of chlorhexidine diacetate and 20 wt % of sodium chloride are mixed together to give a chlorhexidine diacetate-containing polymeric matrix having a 40/60 ratio of high Mw POE-1 to low Mw POE-1.

EXAMPLE 20

To 64 wt % of high Mw POE-1 was added 16 wt % of propylene carbonate (a plasticizer), 20 wt % of metronidazole and 0.25 wt % of sodium carbonate. The mixture was stirred at 37° C. for 20 minutes to give a metronidazole-containing homopolymeric matrix formulation.

EXAMPLE 21

Following the procedure of Example 20, a chlorhexidine diacetate-containing homopolymeric matrix formulation is prepared by combining 48 wt % of high Mw POE-1, 12 wt % of propylene carbonate, 20 wt % of chlorhexidine diacetate and 20 wt % of sodium chloride.

What is claimed is:

1. A composition for delivering a drug into a periodontal pocket of an animal, the composition comprising:
   (a) the drug to be delivered, in a therapeutically effective amount; and
   (b) an oligomeric or polymeric matrix material containing the drug, the matrix material being a less- to non-flowable polymer at or below body temperature and a flowable polymer at a physiologically compatible elevated temperature.

2. A composition according to claim 1 wherein the oligomeric or polymeric matrix material is bioerodible once it is placed in the pocket.

3. The composition of claim 2 wherein the drug is selected from the group consisting of antibiotics, growth factors, anti-inflammatory drugs, antifungals, anti-caries agents and local anesthetics.

4. The composition of claim 2 wherein the drug comprises an antibiotic.

5. The composition of claim 4 wherein the antibiotic comprises tetracycline, minocycline, metronidazole, chorhexidine, sanguinarine, or doxycycline.

6. The composition of claim 2 wherein the matrix material is selected from the group consisting of poly(orthoesters), polylactic acids, polyglycolic acids, polylactides, polyglycolides, polyester oligomers of hydroxycarbonic acids, oligomers of glycolic acid and/or lactic acid and their derivatives with alcohols and/or carbonic acids, and copolymers and mixtures thereof.

7. The composition of claim 2 which further comprises a biocompatible plasticizer.

8. The composition of claim 2 wherein the matrix material is a copolymer of lactic acid and glycolic acid having about 50–75% lactic acid units and about 25–50% glycolic acid units.

9. The composition of claim 2 wherein the matrix material has a dynamic viscosity no greater than about $1\times10^6$ poise at 0.1 radian/second at a physiologically compatible elevated temperature and a dynamic viscosity of greater than about $1\times10^6$ poise at 0.1 radian/second at the body temperature of the tissue pocket.

10. The composition of claim 9 which further comprises a biocompatible plasticizer.

* * * * *